(12) United States Patent
Malmin (10) Patent No.: US 8,143,569 B2
(45) Date of Patent: Mar. 27, 2012

(54) IMAGING SYSTEM AND METHOD FOR TUNING SAME

(75) Inventor: Ronald E. Malmin, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 382 days.

(21) Appl. No.: 12/568,631

(22) Filed: Sep. 28, 2009

(65) Prior Publication Data

US 2010/0080353 A1    Apr. 1, 2010

Related U.S. Application Data

(60) Provisional application No. 61/100,338, filed on Sep. 26, 2008.

(51) Int. Cl.
*G12B 13/00* (2006.01)
(52) U.S. Cl. .................................... 250/252.1
(58) Field of Classification Search ............... 250/252.1, 250/363.09
See application file for complete search history.

(56) References Cited

U.S. PATENT DOCUMENTS

| 5,677,536 | A  | * | 10/1997 | Vickers | 250/363.09 |
| 6,051,830 | A  | * | 4/2000 | Moake | 250/252.1 |
| 2008/0083870 | A1 | * | 4/2008 | Malmin et al. | 250/252.1 |
| 2010/0148046 | A1 | * | 6/2010 | Wang et al. | 250/252.1 |

* cited by examiner

*Primary Examiner* — Mark R Gaworecki
(74) *Attorney, Agent, or Firm* — Peter Kendall (57) ABSTRACT

A method of tuning an imaging system can include the steps of receiving photons at photo-multiplier units that are part of an array, determining an energy level for each of the photo-multiplier units based on events over a specific photo-multiplier unit and determining a sum energy level for the array of photo-multiplier units based on the events over the specific photo-multiplier unit. The method can also include the step of comparing the energy level for each of the photo-multiplier units with the sum energy level for the array of photo-multiplier units to assist in determining a contribution matrix for the array of photo-multiplier units. The energy level determination steps and the comparison step can be repeated for each photo-multiplier unit in the array to determine the contribution matrix.

20 Claims, 8 Drawing Sheets

IMAGING SYSTEM AND METHOD FOR TUNING SAME

FIELD OF TECHNOLOGY

The subject matter herein generally relates to imaging systems and in particular, to tuning such systems.

BACKGROUND OF THE INVENTION

Gamma cameras are primarily used to generate images of organs, bones or other tissues of the body. Typically, a low-level radioactive material is introduced into the body of a patient, which emits gamma rays that can be detected and measured by the gamma camera. Because the radioactive materials are formulated to collect temporarily in a specific part of the body, the emission of the gamma rays can enable a physician to review images of the areas of concern.

A typical gamma camera includes a scintillation crystal, which functions as a detector for the gamma rays from the patient's body. The crystal converts high-energy photons, such as gamma rays and X-rays, into visible light (lower-energy photons). When a gamma ray strikes and is absorbed in the scintillation crystal, the energy of the gamma ray is converted into flashes of light—a large number of scintillation photons—that emanate from the point of the gamma ray's absorption. A photo-multiplier tube (PMT), which is optically coupled to the scintillation crystal, detects a fraction of these scintillation photons and produces an output signal having an amplitude that is proportional to the number of detected scintillation photons. The gamma camera will generally include a two-dimensional array of PMTs, each capable of generating the proportional output signals. After a gamma ray absorption event, the outputs from the PMTs can be processed to determine the location of the absorption event.

In particular, the number of scintillation photons producing electrical signals in each PMT falls rapidly as the distance of the PMT from the point of gamma ray absorption, or event location, increases. The position of the event is typically calculated from an appropriately weighted centroid of the signals from the PMTs surrounding the event location.

Ideally, the total energy of a given gamma ray measured anywhere on the camera should have the same value. To achieve this principle, the gains of the PMTs must be matched (the camera must be "tuned"). Notably, the amplitudes of the signals derived from each PMT are proportional to two basic factors: 1) the number of scintillation photons detected by a PMT; and 2) the gain or amplification of the PMT.

As part of the tuning procedure, the gains of the PMTs are adjusted such that the sum of the output signals from all the PMTs are roughly equal in response to a fixed energy gamma event, regardless of the location of the event. The process of tuning a gamma camera relies on the knowledge of a contribution matrix. Prior art processes of determining the contribution matrix (using only a total energy signal) are tedious and time-consuming, and small matrix elements for them are poorly defined. Thus, in view of the difficulty in obtaining a contribution matrix, a generic contribution matrix is typically used for tuning conventional gamma cameras. A generic contribution matrix is normally an average of contribution matrices developed for several gamma cameras.

This generic matrix may be suitable for PMTs that are within the interior of the array in which they are positioned. Variation in the light collection at PMTs near the edges of the array, however, causes significant disparities in matrix elements for these PMTs. As such, the use of a generic contribution matrix bogs down the tuning process.

SUMMARY OF THE INVENTION

A method of tuning an imaging system is described herein. The method can include the steps of receiving photons at photo-multiplier units that are part of an array, determining an energy level for each of the photo-multiplier units based on events over a specific photo-multiplier unit and determining a sum energy level for the array of photo-multiplier unit based on the events over the specific photo-multiplier unit. The method can also include the step of comparing the energy level for each of the photo-multiplier units with the sum energy level for the array of photo-multiplier units to assist in determining a contribution matrix for the array of photo-multiplier units.

The method can also include the step of performing the determination of the energy level for each of the photo-multiplier units, the determination of the sum energy level for the array of photo-multiplier units and the comparison of the two energy levels for each photo-multiplier unit in the array to determine the contribution matrix. The method can also include the step of generating the inverse of the contribution matrix.

The inverse of the contribution matrix can be used to tune an imaging system. As such, the method can further include the step comparing updated sum energy levels for the array of photo-multiplier units that are determined for each photo-multiplier unit in the array with a reference value to determine a measurement error value for each photo-multiplier unit in the array. The method can also include the step of determining the product of the inverse of the contribution matrix with the measurement error values for the photo-multiplier units in the array to determine a gain change for each photo-multiplier unit in the array to produce a uniform total event energy over the entire array of photo-multiplier units. Based on the determined gain changes, the gains of the photo-multipliers can be adjusted.

In one arrangement, the imaging system can be a gamma camera that detects gamma rays. Also, at least a portion of the received photons can be within the visible light spectrum.

An imaging system is also described herein. The imaging system can include a detection crystal that can receive and absorb high-energy photons from a test source and can convert the high-energy photons into low-energy photons. The system can further include an array of photo-multiplier units optically coupled to the detection crystal in which the photo-multiplier units are configured to detect the low-energy photons. The system can also have an electronics module that can be coupled to the array of photo-multiplier units. The module can be operable to—in response to events over a first photo-multiplier unit—determine an energy level for each of the photo-multiplier units of the array corresponding to the events over the first photo-multiplier unit and determine a sum energy level for the array of photo-multiplier units that can also correspond to the events over the first photo-multiplier unit. The system can also include a processor coupled to the electronics module in which the processor can be operable to compare the energy level for each of the photo-multiplier units with the sum energy level for the array of photo-multiplier units for generating a contribution matrix for the array of photo-multiplier units.

In one arrangement, the electronics module can be further operable to determine an energy level for each of the photo-multiplier units based on events over each of the remaining photo-multiplier units in the array and to determine a sum energy level for the array based on events over each of the remaining photo-multiplier units in the array for the contribution matrix. In addition, the processor can be further operable to generate the inverse of the contribution matrix. As noted earlier, this inverse matrix can be used to tune the imaging system.

As such, the processor can be further operable to compare updated sum energy levels based on events over the first photo-multiplier unit and events over the remaining photo-multiplier units with a reference value to determine a measurement error value for each of the photo-multiplier units of the array. In another arrangement, the processor can be further operable to calculate a gain change for each photo-multiplier unit in the array, using the inverse of the contribution matrix and the measurement error values.

The system can also include an adjustment mechanism that can be configured to adjust the gains of the photo-multiplier units based on the gain changes to produce a uniform total event energy over the entire array of photo-multiplier units. As an example, the high-energy photons can be gamma rays or X-rays and at least a portion of the low-energy photons can be within the spectrum of visible light. As another example, the detection crystal can be a scintillation crystal.

Another imaging system is described herein. This system can include means for receiving gamma rays and converting the gamma rays into flashes of light and means for detecting the flashes of light and converting the detected flashes of light into signals for processing. The means can be optically coupled to the means for receiving gamma rays and can form an array and can include individual detection elements. The system can further include means for determining an energy level for each of the individual elements and the entire array in response to events over an individual detection element and means for comparing the energy level for each of the individual elements and the array and for generating a contribution matrix for the array based on the comparison.

In one arrangement, the comparing means can also be for generating an inverse of the contribution matrix and measurement error values based on energy levels. The comparing means can also be for calculating a gain change for each individual element in the array based on the inverse of the contribution matrix and the measurement error values. The system can also have means for adjusting the gain of the individual elements in the array based on the calculated gain changes.

BRIEF DESCRIPTION OF THE DRAWINGS

Embodiments of the present description will now be described, by way of example only, with reference to the attached Figures, wherein.

DETAILED DESCRIPTION OF THE INVENTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein.

Several definitions that apply throughout this document will now be presented. The word "couple" or "coupled" is defined as to be connected, although not necessarily in a mechanical sense. The term "photo-multiplier unit" is a component that detects light, converts the light into an electrical signal and amplifies the signal. The term "array of photo-multiplier units" is defined as any ordered positioning of a plurality of photo-multiplier units. A "reference value" is defined as any value that is predetermined and is used to determine errors or variations in measurements. A "gamma camera" is defined as any component or group of components that is used to image gamma radiation emitting radioisotopes. The term "visible light spectrum" means light that has a wavelength from approximately 380 nanometers (nm) to approximately 750 nm. A "low-energy photon" is defined as one that has a frequency within the visible light spectrum or one that has a wavelength within the ultraviolet range, from around roughly 10 nm to 380 nm. A "high-energy photon" means one that has a wavelength that is shorter than that found in the ultraviolet range, or less than about 10 nm.

A "detection crystal" is defined as any component or group of components that is capable of receiving and absorbing particles of energy and reemitting the absorbed energy as light, either within or outside the visible light spectrum. The term "electronics module" is defined as a component or a group of components that is able to determine energy levels for photo-multiplier units in an array based on an event. A "processor" is defined as a component or a group of components that is capable of executing or conducting any of the processes described herein. Further definitions may be presented below.

As noted earlier, there are shortcomings in determining a contribution matrix for gamma cameras for purposes of tuning these cameras. Current methods rely on a generic contribution matrix, which is less accurate for PMTs at the edges of a PMT array and slows down the tuning process. A method of tuning an imaging system that overcomes these disadvantage is presented here The method can include the steps of receiving photons at photo-multiplier units that are part of an array, determining an energy level for each of the photo-multiplier units based on events over a specific photo-multiplier unit and determining a sum energy level for the array of photo-multiplier units based on the events over the specific photo-multiplier unit. The method can also include the step of comparing the energy level for each of the photo-multiplier units with the sum energy level for the array of photo-multiplier units to assist in determining a contribution matrix for the array of photo-multiplier units. The energy level determination steps and the comparison step can be repeated for each photo-multiplier unit in the array to determine the contribution matrix. This process can quickly and efficiently provide a contribution matrix, which can accurately describe the light transport properties (optics) of the specific detector being measured. This customized contribution matrix can be used to more efficiently adjust the gain of the photo-multiplier units in the array and speed the tuning process.

Figure 1:
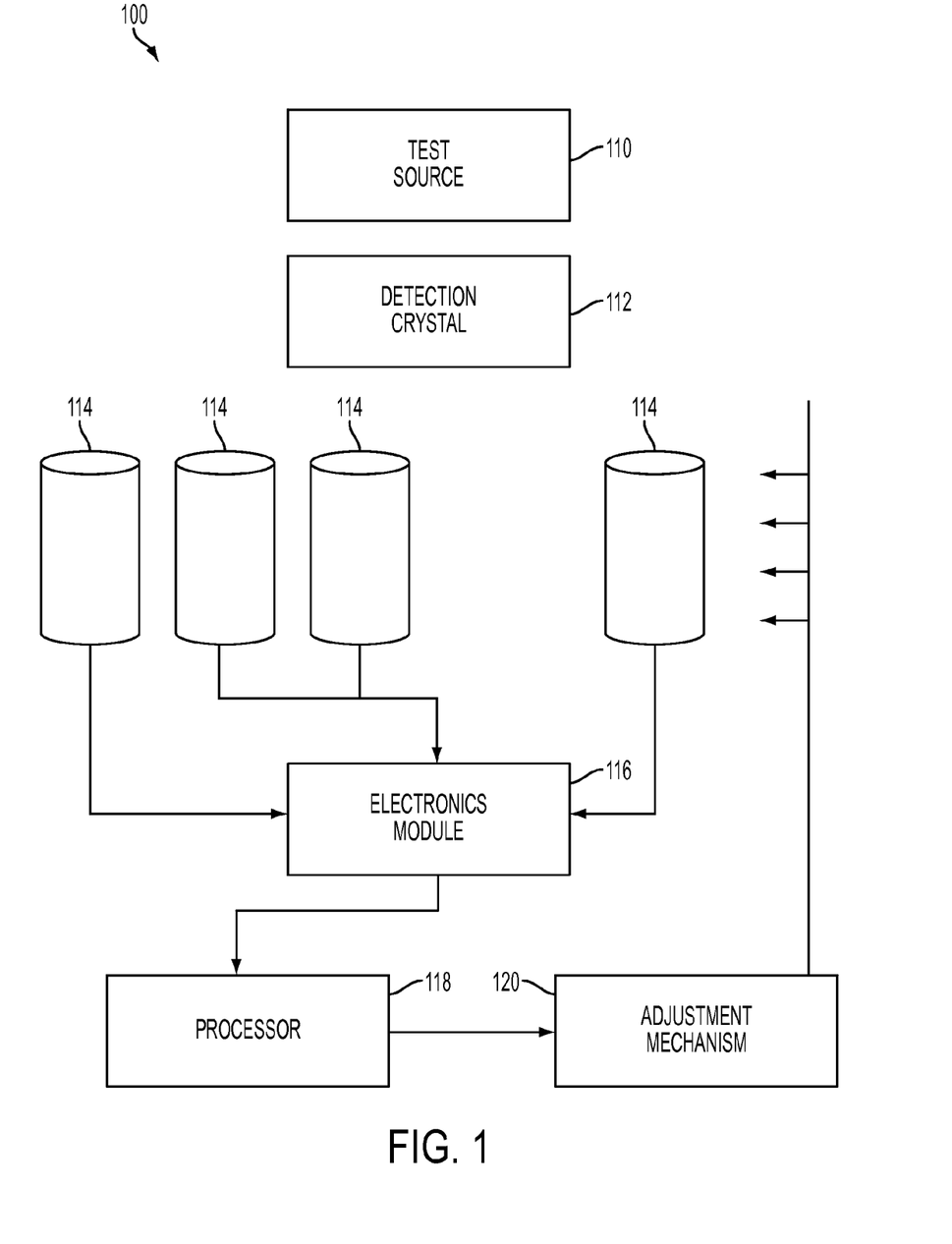
FIG. 1 illustrates an example of an imaging system.

Referring to FIG. 1, an example of an imaging system 100 is shown. In one arrangement, the imaging system 100 can be a gamma camera or at least part of a gamma camera, although the structures and processes described herein are not so limited. The system 100 can include a test source 110, a detection crystal 112 and an array of photo-multiplier units 114 that are optically coupled to the detection crystal 112. The term "optically coupled" is defined as any connection that enables the passage of electromagnetic radiation between two components and may include the use of physical components. The detection crystal 112 may receive, for example, high-energy photons during an examination of a patient and convert them into low-energy photons, such as flashes of light. An example of a detection crystal 112 is a scintillation crystal. As another example, the photo-multiplier unit 114 may be a PMT, although other suitable light-to-electrical output components may be used. Although not meant to be limiting, when describing the operation of the system 100, the term photomultiplier tube 114 or PMT 114 will be used.

The test source 110 can be any suitable material for directing photons, such as high-energy photons, towards the detection crystal 112 in a fairly uniform manner. Additionally, the detection crystal 112 can convert the photons from the test source 110 into low-energy photons, which can generate flashes of light that can be detected by the PMTs 114. The PMTs 114 can generate and amplify signals that correspond to the detected flashes of light.

The system 100 can also include an electronics module 116 and a processor 118. As will be explained below, the electronics module 116 can receive the output signals from the PMTs 114 and can generate a spectrum for each PMT 114 showing the energy level associated with a flash of light substantially centered over a particular PMT 114. The electronics module 116 can also generate a set of spectra for the entire array of PMTs 114 based on this light that was substantially centered over a particular PMT 114. These spectra can be fed to the processor 118, which can compare the energy values to generate a fractional value for each PMT 114 that effectively indicates the relative amount of light detected by each PMT 114 for the light centered over the relevant PMT. The processor 118 can determine a matrix of these fractional values, which can then be used to determine gain changes for the PMTs 114. Specific examples of this process will be described below.

Once the gain changes are determined, the processor 118 can signal the adjustment mechanism 120 to adjust the gain on one or more of the PMTs 114. As an example, the adjustment mechanism 120 can be a circuit that can be coupled to each of the PMTs 114 and that can be capable of selectively adjusting the voltage gain on each of the PMTs 114.

Figure 2:
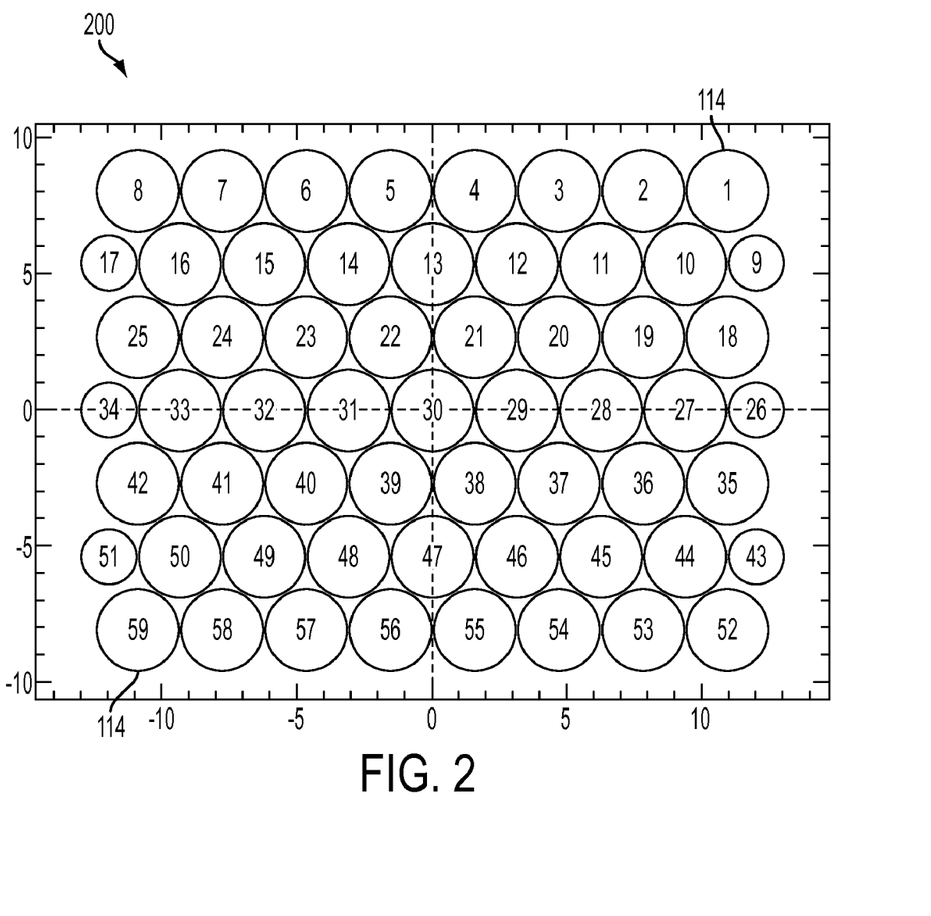
FIG. 2 illustrates an example of a PMT array.
Figure 3A:
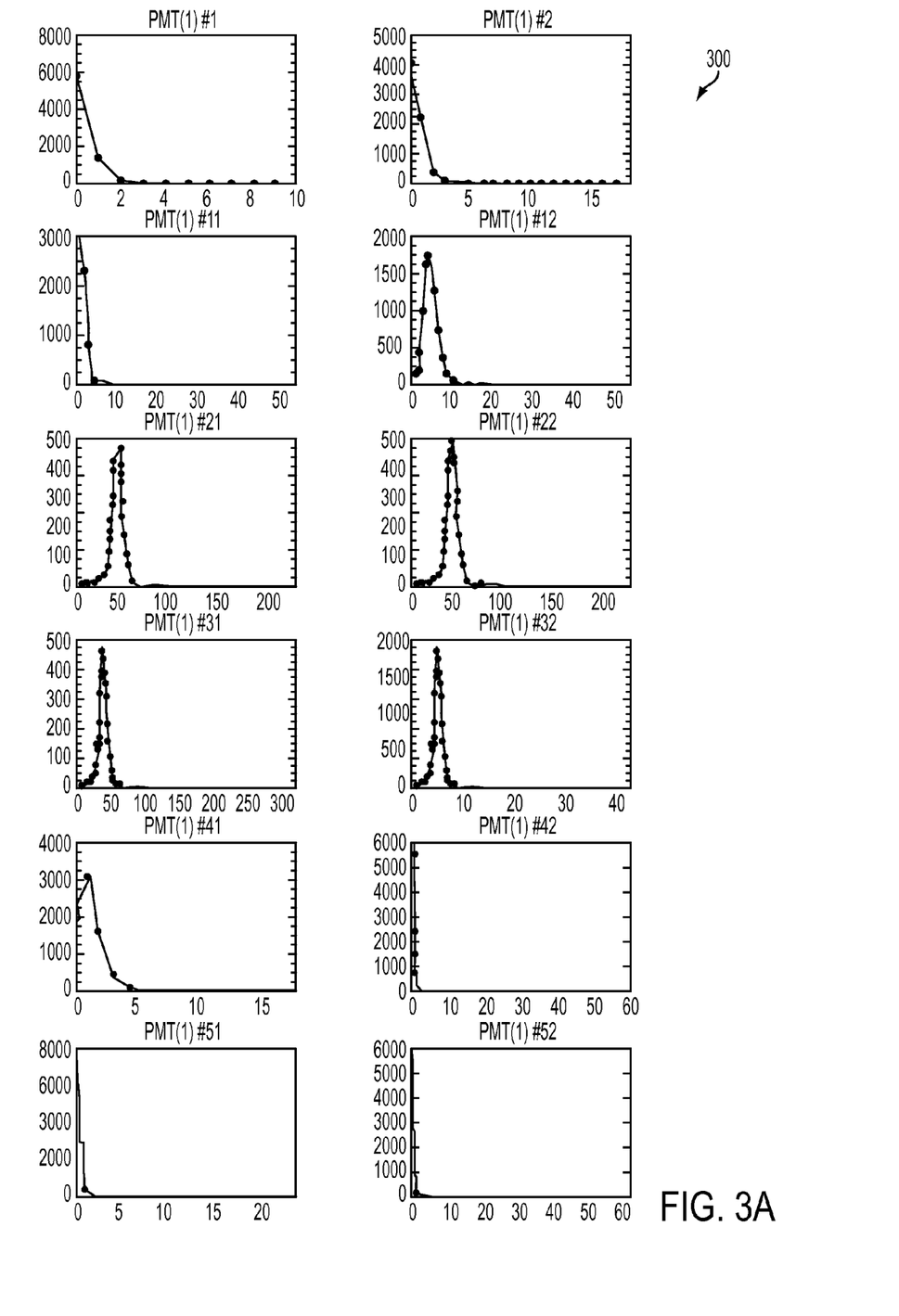
FIG. 3 illustrates an exemplary set of energy spectra for the PMT array of FIG. 2.
Figure 3B:
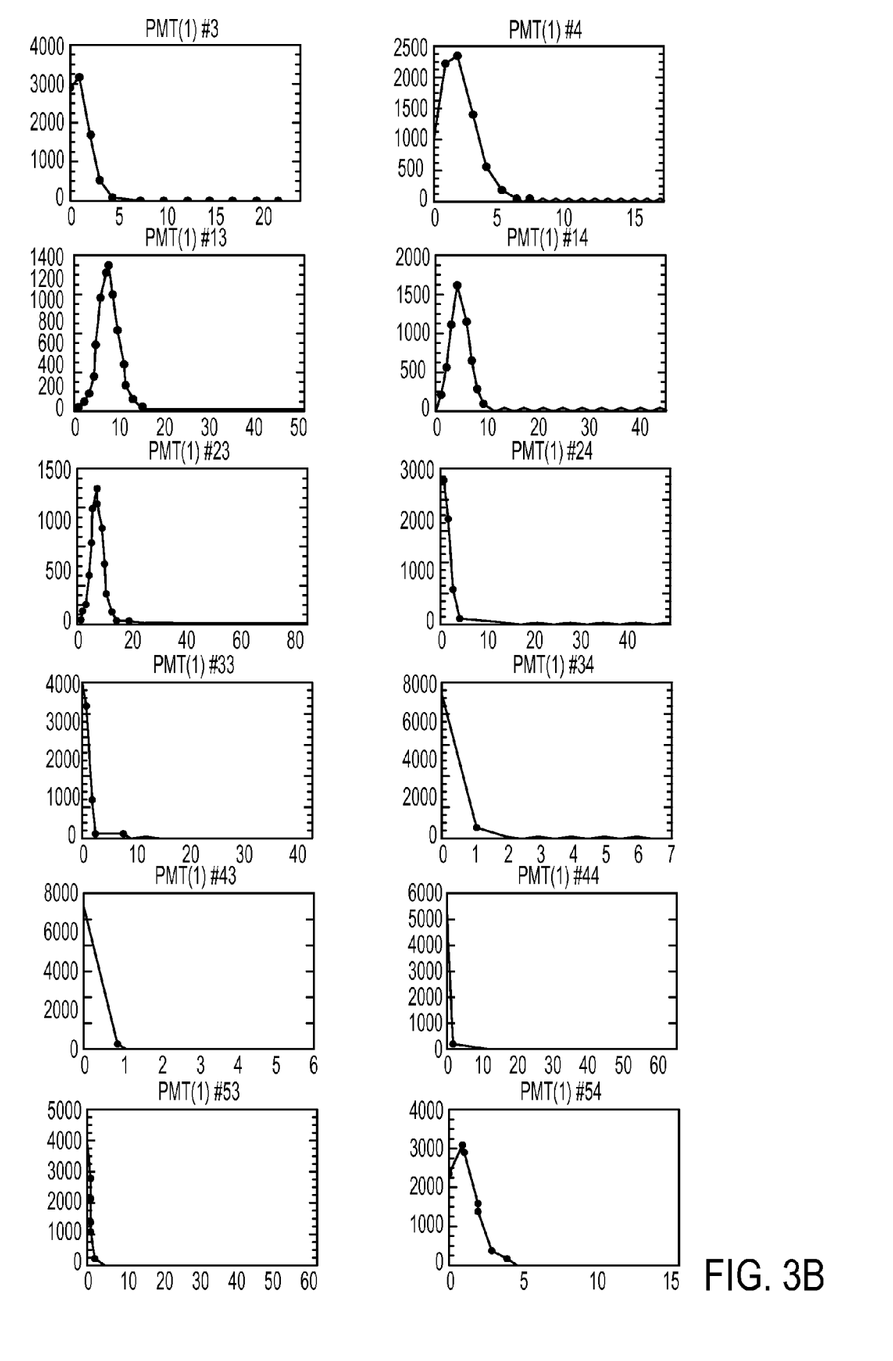
Figure 3C:
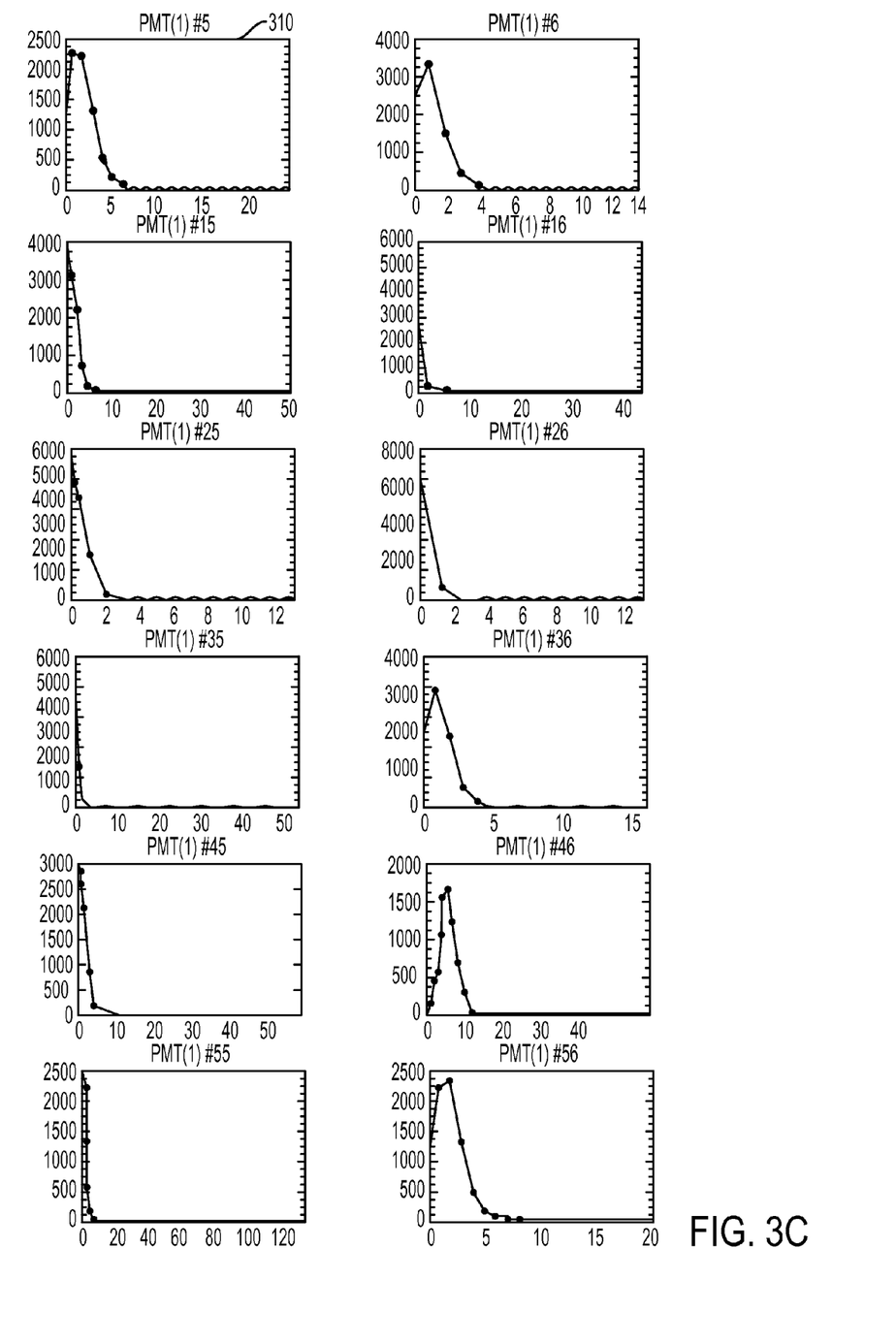
Figure 3D:
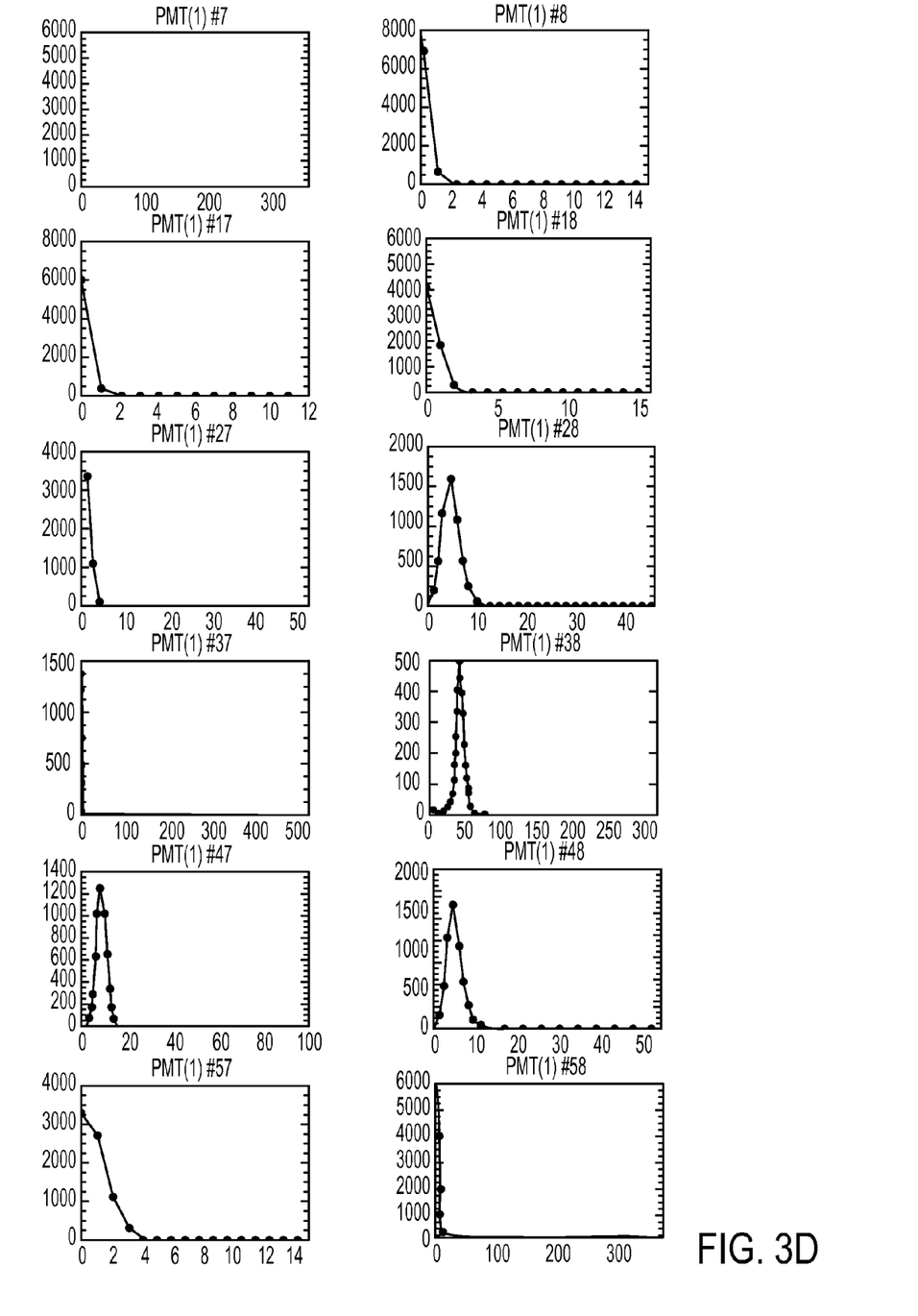
Figure 3E:
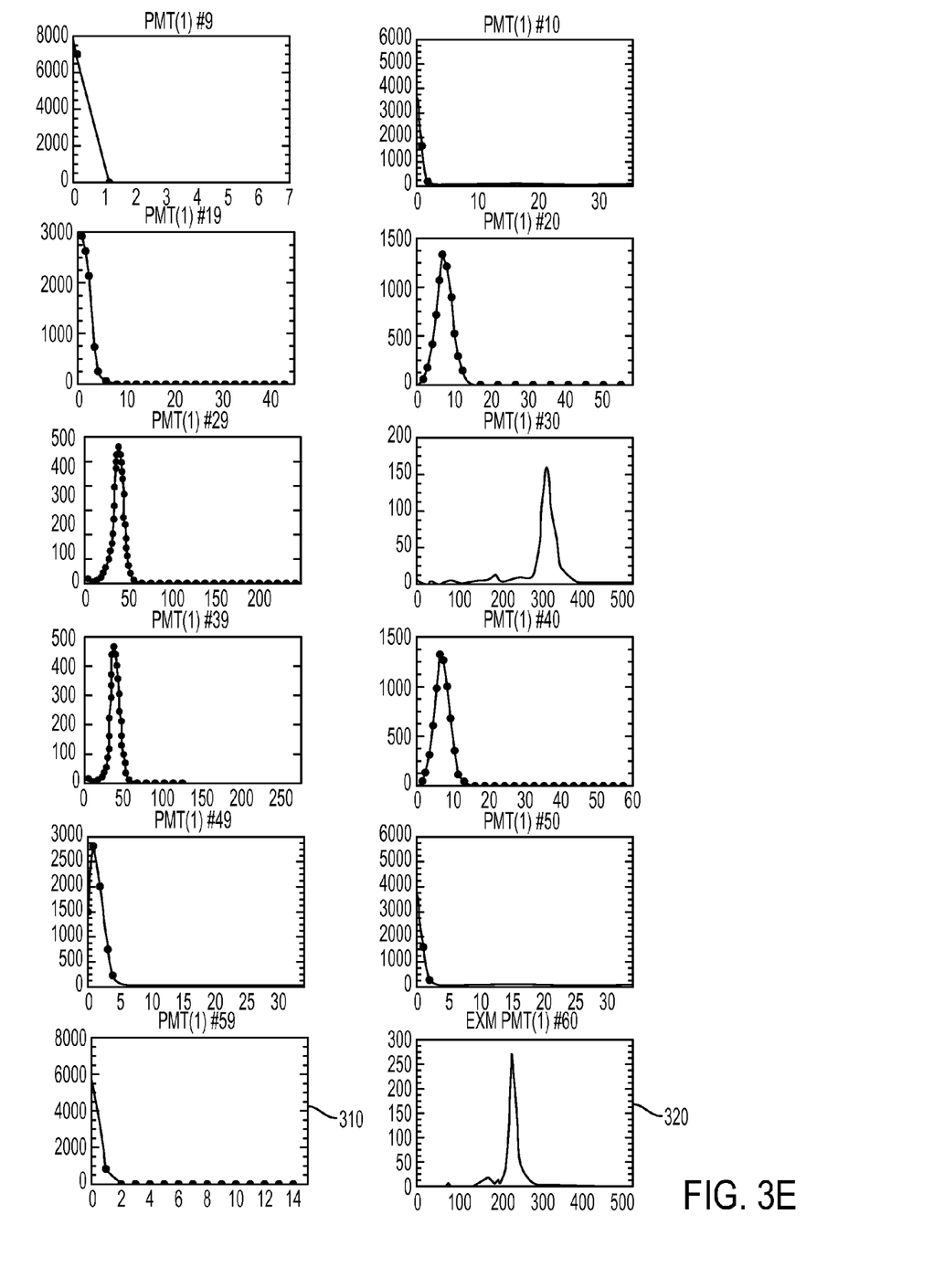

Referring to FIG. 2, an example of an array 200 of PMTs 114 is shown. In this exemplary array 200, a total of fifty-nine PMTs 114 are pictured. It must be understood, however, that the array 200 is not so limited, as the array 200 can include any suitable number of PMTs 114. Moreover, the array 200 is not limited to the particular positioning shown in FIG. 2, and the PMTs 114 are not necessarily limited to the geometric configurations depicted here.

As explained earlier, these PMTs 114 detect light flashes and convert them into electrical signals. The electronics module 116 and the processor 118 can determine where the light flashes occur over the array 200 and whether they occur substantially over the center of a PMT 114. In one arrangement, light flashes that do not occur substantially over the center of a PMT 114 can be ignored for processing. For example, assume a low-energy photon is emitted from the detection crystal 112 (see FIG. 1), and this results in a flash of light being substantially centered over the PMT 114 with a designation of "30." This energy that is substantially centered or predominately over a PMT 114 is referred to as an "event." PMT (30) can then generate an output signal that corresponds to the amount of light that it detects from the light. Moreover, the other PMTs 114 in the array 200 may also detect some of the light from the event, even though it was predominately over PMT (30). This principle is particularly true for the PMTs 114 that surround PMT (30), such as the PMTs 114 with designations of "21," "22," "31," and so on. As such, these PMTs 114 can generate output signals based on the event above PMT (30). In fact, it is possible that each of or at least a substantial majority of the PMTs 114 in the array 200 can detect light from the event over PMT (30) and can generate an output signal that corresponds to the level of detection.

In addition to the detection and processing of the individual output signals from the PMTs 114 in response to an event, the total energy from the event can be determined. For example, the output signals from the PMTs 114 of the array 200 can be summed together to create a total energy signal that represents the total amount of detected energy by the entire array 200 in view of the event over a particular PMT 114.

Also, because the test source 110 is essentially flooding the system 100 with photons, the system 100 can identify flashes of light that are centered over each of the other PMTs 114, which can result in individual energy signals from the other PMTs 114 and total energy signals from the array 200. For example, consider another event over PMT (23). In response, PMT (23) and the other PMTs 114 can generate output signals that are indicative of the amount of light individually detected by the PMTs 114 from the event. Similar to the previously described example, a total energy signal from the entire array 200 based on the event above PMT (23) can be determined. As will be explained below, these signals can be used to assist in building a contribution matrix.

Referring to FIG. 3, an example of multiple energy spectra 300 is shown. Reference will be made to FIG. 2 to describe the energy spectra 300. Each graph 310 can correspond to the amount of energy detected by a PMT 114 in the array 200 and is labeled at the top with the appropriate PMT number. There is also a single graph 320 that can represent the total amount of energy detected by the entire array 200 of PMTs 114 (the summation of all the output signals for an event over a particular PMT 114). The horizontal axis for each of the graphs 310, 320 represents the magnitude of the energy (number of light photons) detected in that PMT 114 for a scintillation event located over another particular PMT 114—in this case PMT (30). The vertical axis plots the number of events detected with that amount of energy.

The energy spectra 300 are associated with events over PMT (30), a process that was described above. That is, each of the graphs 310 shows the distribution (histogram) of energies detected in each PMT 114 in the array 200 for a large number of events substantially centered over PMT (30). In addition, the graph 320 shows the total energy detected by the entire array 200 for the event over PMT (30). This process is stochastic, so the distribution of energies (spectral peaks) are Gaussian for PMTs with large signals (such as PMTs (28-32) and (20-23)) and Poisson (asymmetric) for PMTs 114 with small signals (such as PMTs that are farther away from the events). In view of the other PMTs 114 in the array 200, energy spectra can be generated for events over each remaining PMT 114, which may be similar to what is pictured in FIG. 3 for PMT (30). It must be noted that the values that are shown in the graphs 310, 320 are merely exemplary in nature and are not intended to be limiting. Moreover, as pointed out earlier, the description here is not limited to the particular array 200 shown in FIG. 2.

Figure 4:
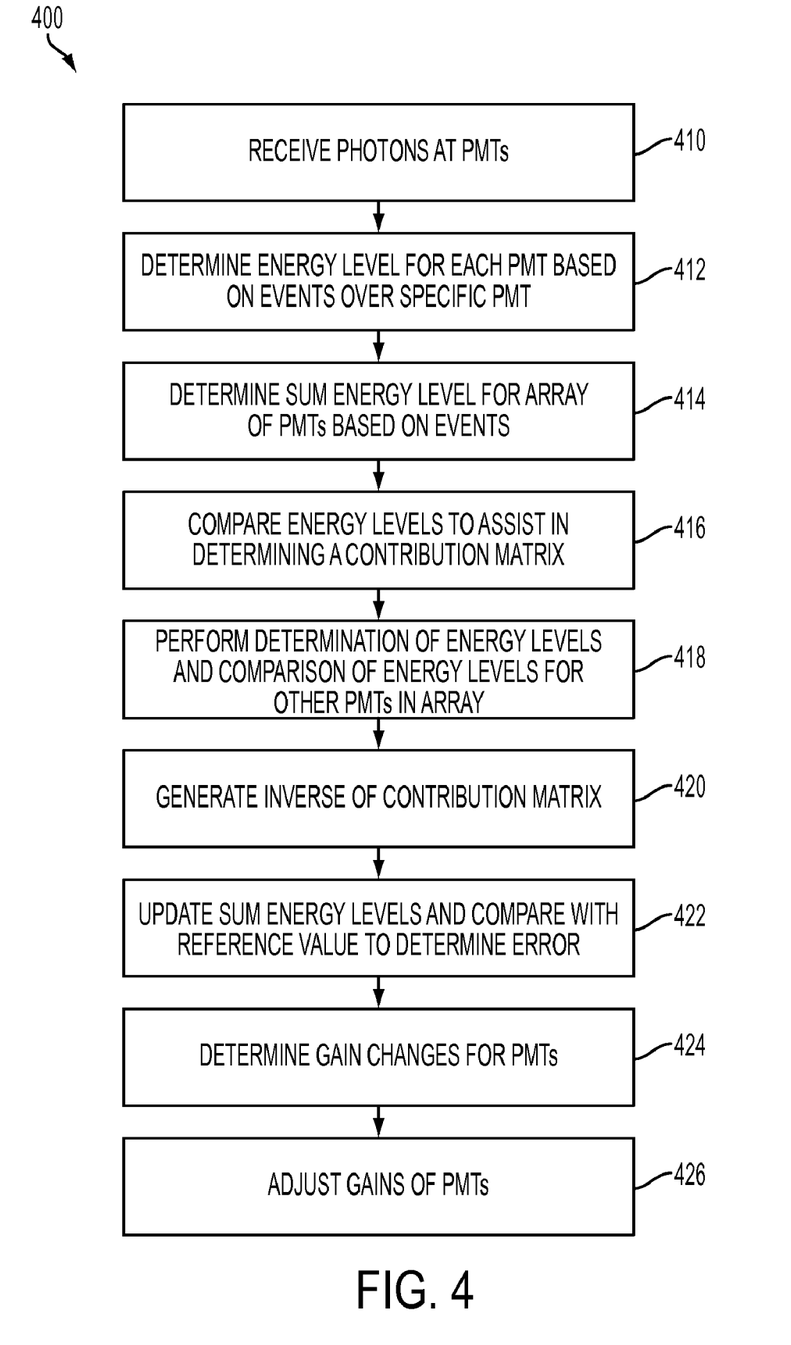
FIG. 4 illustrates an example of a method of tuning an imaging system.

Referring to FIG. 4, an example of a method 400 of tuning an imaging system is shown. When describing this method 400, reference can be made to the system 100 of FIG. 1, the array 200 of FIG. 2 and the spectra 300 of FIG. 3, although it is understood that the method 400 can be practiced with any other suitable system and PMT array and can generate other suitable spectra. Moreover, it must be noted that the method 400 is not necessarily limited to the steps shown here, as the method 400 can contain a greater or fewer number of steps in comparison to what is pictured. The method 400 is not necessarily limited to the particular ordering shown here, either.

In one arrangement, the method 400 can represent two different acquisition modes: (1) creation of a contribution matrix; and (2) tuning an imaging system. As will be described, the contribution matrix can be generated and can be used to help tune the imaging system.

At step 410, photons can be received at PMTs that are part of an array, and an energy level can be determined for each of the PMTs based on events over a specific (or first) PMT, as shown at step 412. At step 414, a sum energy level can be determined for the array of PMTs based on the events over the specific PMT. In addition, the energy level for each of the PMTs can be compared with the sum energy level for the array of PMTs, which can assist in determining a contribution matrix for the array of PMTs, as shown at step 416. At step 418, the determination steps 412, 414 and the comparison step 416 can be performed for each PMT in the array to determine the contribution matrix. At step 420, the inverse of the contribution matrix can be generated, which can be saved for use in tuning the imaging system.

At step 422, the sum energy levels for the array of PMTs that are determined for each PMT in the array can be updated and compared with a reference value to determine a measurement error value for each PMT in the array. The product of the inverse of the contribution matrix and the measurement error values for the PMTs in the array can be determined, which can produce a gain change for each PMT in the array that would result in a uniform total energy event over the entire array of PMTs, as shown at step 424. At step 426, the gains of the PMTs can be adjusted based on the gain changes.

An example will be presented to help explain this method. In particular, reference will be made to the events over the PMT (30) that produced the spectra 300 in FIG. 3. The photons from these events can be received at the PMTs 114 of the array 200, and the electronics module 116 can determine an energy level for each of the PMTs 114 in the array 200 based on this event. An example of this process is depicted in the graphs 310 of FIG. 3. The electronics module 116 can also determine a sum energy level for this event, which can be the result of the sum of all the individual output signals from the PMTs 114 of the array 200. An example of such is presented in graph 320 of FIG. 3. As explained earlier, the generation of these spectra can be based on events that occur substantially over the center of a particular PMT 114. Further, for each event, an event counter in the electronic module 116 can be incremented. This count can be used to determined whether a sufficient number of events have occurred for processing to take place. As the events are tracked, the electronics module 116, by updating the spectra, can update the energy levels that are shown in graphs 310 and 320.

After a sufficient number of events have been processed, the processor 118 can determine the mean energy (peak center) for each spectra 310 associated with a given summed event energy spectra 320. This process can be repeated for all summed event spectra. The processor 118, at this point, can compare the energy level for each PMT 114 with the sum energy level to determine the fractional value of the energy detected by each PMT 114 from the events over PMT (30) in relation to the total energy for the array 200 from the events.

In other words, the processor 118 can compare the energy levels of each graph 310 with the graph 320, as shown in FIG. 3 for the events, which can be the ratio of the peak center for a particular PMT 114 associated with events over a PMT 114 divided by the peak center in the summed energy spectrum. The fractional value that is determined for each PMT 114 in relation to the total energy of the events over PMT (30) can be part of a contribution matrix.

Fractional values can also be determined for events over the remaining PMTs 114. To do so, the processor 118 can compare the individual energy levels for each PMT 114 with the sum energy level based on events over the remaining PMTs 114, as described above. For example, assume events are substantially centered over PMT (23). Energy levels can be determined for each of the PMTs 114 based on this event, as well as a sum energy level for the entire array 200. The processor 118 can then compare each of the individual energy levels with the sum energy level to determine a fractional value for each of the PMTs 114 based on the events over PMT (23). These fractional values can also be part of the contribution matrix. In this exemplary array 200, the contribution matrix can be a 59×59 matrix. Thus, because of access to the output signals of the individual PMTs 114, the contribution matrix can be generated much faster and easier than in prior art systems. As previously noted, this contribution matrix can assist in tuning of the imaging system 100.

As part of the tuning process, the electronic module 116 can update the summed energy event spectrum associated with events over a certain PMT 114. After a sufficient number of events have been processed, the processor 118 can determine the mean energy (peak center) for each summed event energy spectrum 320. The processor 118 can compare the summed event energies for each PMT 114 in the array 200 with a reference value to determine the error in the summed energy value for each PMT 114 in the array 200. The processor 118 can perform this operation for all the other PMTs in the array 200 to generate multiple measurement error values, which can be in the form of a summed energy error matrix.

Continuing with the tuning process, the processor 118 can also determine the product of the inverse of the contribution matrix with the plurality of measurement error values (or the summed energy error matrix). This product can be related to gain changes in the PMTs 114 of the array 200, and thus, it can be used to determine a gain change for each PMT 114 in the array 200. Specifically, if the energies are close to the reference value and if the contribution matrix accurately describes the light transport of the optics of the imaging system 100, the gain changes can result in a uniform total energy event over the entire array 200. It is possible that inaccuracies in the contribution matrix may lead to imprecise gain changes. Nevertheless, repetition of this process can eventually result in sufficiently small errors. As described above, however, accurate determination of the contribution matrix can speed the convergence to a tuned system. Once the gain changes are determined, the processor 118 can signal the adjustment mechanism 120, which can process the gain changes to determine which PMTs 114 require adjustment.

Portions of the system 100 and supporting components can take the form of hardware elements, software elements or elements containing both hardware and software. In one embodiment, the software portions can include, but are not limited to, firmware, resident software, microcode, etc. Furthermore, these software portions can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium (though propagation mediums in and of themselves as signal carriers are not included in the definition of physical computer-readable medium). Examples of a physical computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. Both processors and program code for implementing each as aspect of the system can be centralized or distributed (or a combination thereof) as known to those skilled in the art.

A data processing system suitable for storing program code and for executing program code, which can be implemented in any of the above-referenced devices described herein, can include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. I/O devices (including but not limited to keyboards, displays, pointing devices, etc.) can be coupled to the system either directly or through intervening I/O controllers.

Examples have been described above regarding an imaging system and method of tuning same. One of ordinary skill in the art, however, will appreciate that the method can be implemented in other suitable systems. In addition, various modifications to and departures from the disclosed embodiments will occur to those having skill in the art. The subject matter that is intended to be within the spirit of this disclosure is set forth in the following claims.

What is claimed is:

1. A method utilizing a processor for tuning an imaging system, comprising:
   receiving photons at photo-multiplier units that are part of an array;
   determining an energy level for each of the photo-multiplier units based on events over a specific photo-multiplier unit;
   determining a sum energy level for the array of photo-multiplier unit based on the events over the specific photo-multiplier unit; and
   comparing the energy level for each of the photo-multiplier units with the sum energy level for the array of photo-multiplier units to assist in determining a contribution matrix for the array of photo-multiplier units.

2. The method according to claim 1, further comprising performing the determination of the energy level for each of the photo-multiplier units, the determination of the sum energy level for the array of photo-multiplier units and the comparison of the two energy levels for each photo-multiplier unit in the array to determine the contribution matrix.

3. The method according to claim 2, further comprising generating the inverse of the contribution matrix.

4. The method according to claim 3, further comprising comparing updated sum energy levels for the array of photo-multiplier units that are determined for each photo-multiplier unit in the array with a reference value to determine a measurement error value for each photo-multiplier unit in the array.

5. The method according to claim 4, further comprising determining the product of the inverse of the contribution matrix with the measurement error values for the photo-multiplier units in the array to determine a gain change for each photo-multiplier unit in the array to produce a uniform total event energy over the entire array of photo-multiplier units.

6. The method according to claim 5, further comprising adjusting the gains of the photo-multipliers based on the determined gain changes.

7. The method according to claim 1, wherein the imaging system is a gamma camera that detects gamma rays.

8. The method according to claim 1, wherein at least a portion of the received photons are within the visible light spectrum.

9. An imaging system, comprising:
   a detection crystal that receives and absorbs high-energy photons from a test source and converts the high-energy photons into low-energy photons;
   an array of photo-multiplier units optically coupled to the detection crystal, wherein the photo-multiplier units are configured to detect the low-energy photons;
   an electronics module that is coupled to the array of photo-multiplier units, wherein the electronics module is operable to:
      in response to events over a first photo-multiplier unit, determine an energy level for each of the photo-multiplier units of the array corresponding to the events over the first photo-multiplier unit;
      determine a sum energy level for the array of photo-multiplier units that also corresponds to the events over the first photo-multiplier unit; and
   a processor coupled to the electronics module, wherein the processor is operable to compare the energy level for each of the photo-multiplier units with the sum energy level for the array of photo-multiplier units for generating a contribution matrix for the array of photo-multiplier units.

10. The imaging system of claim 9, wherein the electronics module is further operable to determine an energy level for each of the photo-multiplier units based on events over each of the remaining photo-multiplier units in the array and to determine a sum energy level for the array based on events over each of the remaining photo-multiplier units in the array for the contribution matrix.

11. The imaging system according to claim 10, wherein the processor is further operable to generate the inverse of the contribution matrix.

12. The imaging system according to claim 11, wherein the processor is further operable to compare updated sum energy levels based on events over the first photo-multiplier unit and events over the remaining photo-multiplier units with a reference value to determine a measurement error value for each of the photo-multiplier units of the array.

13. The imaging system according to claim 12, wherein the processor is further operable to calculate a gain change for each photo-multiplier unit in the array, using the inverse of the contribution matrix and the measurement error values.

14. The imaging system according to claim 13, further comprising an adjustment mechanism that is configured to adjust the gains of the photo-multiplier units based on the gain changes to produce a uniform total event energy over the entire array of photo-multiplier units.

15. The imaging system according to claim 9, wherein the high-energy photons are gamma rays or X-rays and at least a portion of the low-energy photons are within the spectrum of visible light.

16. The imaging system according to claim 9, wherein the detection crystal is a scintillation crystal.

17. An imaging system, comprising:
  means for receiving gamma rays and converting the gamma rays into flashes of light;
  means for detecting the flashes of light and converting the detected flashes of light into signals for processing, wherein the means is optically coupled to the means for receiving gamma rays and forms an array and includes individual detection elements;
  means for determining an energy level for each of the individual elements and the entire array in response to events over an individual detection element; and
  means for comparing the energy level for each of the individual elements and the array and for generating a contribution matrix for the array based on the comparison.

18. The imaging system according to claim 17, wherein the comparing means is also for generating an inverse of the contribution matrix and measurement error values based on energy levels.

19. The imaging system according to claim 18, wherein the comparing means is also for calculating a gain change for each individual element in the array based on the inverse of the contribution matrix and the measurement error values.

20. The imaging system according to claim 19, further comprising means for adjusting the gain of the individual elements in the array based on the calculated gain changes.

* * * * *